US006593142B2

(12) United States Patent
Kelly et al.

(10) Patent No.: US 6,593,142 B2
(45) Date of Patent: Jul. 15, 2003

(54) POLYMERIC FOOD SPOILAGE SENSOR (75) Inventors: Craig A. Kelly, Ellicott City, MD (US); George M. Murray, Columbia, MD (US); O. Manuel Uy, Ellicott City, MD (US)

(73) Assignee: The Johns Hopkins University, Baltimore, MD (US)

(*) Notice: Subject to any disclaimer, the term of this patent is extended or adjusted under 35 U.S.C. 154(b) by 95 days.

(21) Appl. No.: 10/019,763
(22) PCT Filed: Apr. 9, 2001
(86) PCT No.: PCT/US01/11701
§ 371 (c)(1), (2), (4) Date: Oct. 26, 2001
(87) PCT Pub. No.: WO01/77667
PCT Pub. Date: Oct. 18, 2001

(65) Prior Publication Data
US 2003/0100118 A1 May 29, 2003

Related U.S. Application Data
(60) Provisional application No. 60/195,934, filed on Apr. 10, 2000.

(51) Int. Cl.$^7$ ............................................. G01N 33/02
(52) U.S. Cl. ................... 436/1; 436/164; 422/61; 422/58; 426/232; 116/206; 424/9.2; 424/10.3
(58) Field of Search .................... 436/1, 164, 166, 436/168–169, 814; 422/58, 61, 56; 426/232; 116/206; 424/9.1, 9.2, 10.3

(56) References Cited

U.S. PATENT DOCUMENTS

| | | | | |
|---|---|---|---|---|
| 2,485,566 A | * | 10/1949 | Clark | 435/29 |
| 3,067,015 A | * | 12/1962 | Lawdermilt | 422/56 |
| 5,188,816 A | * | 2/1993 | Sherry et al. | 424/9.363 |
| 5,306,466 A | * | 4/1994 | Goldsmith | 422/58 |
| 5,653,941 A | * | 8/1997 | Veretto et al. | 422/58 |
| 6,225,132 B1 | * | 5/2001 | Drukier et al. | 436/541 |

* cited by examiner

Primary Examiner—Lyle A. Alexander
(74) Attorney, Agent, or Firm—Francis A. Cooch (57) ABSTRACT

A polymeric food spoilage sensor comprises a polymer containing a polyazamacrocyclic transition metal complex. The complex selectively binds biogenic amines, such as cadaverine, putrescine and histamine, which are released by food spoilage microorganisms. The polymer undergoes a detectable color change upon exposure to biogenic amine, thus indicating that food spoilage has probably occurred. In one embodiment, the polymer is molecularly imprinted with the biogenic amine to impart selective binding affinity. The polymer is easily incorporated in common food containers and can be employed in fiber optic detection devices.

27 Claims, 3 Drawing Sheets

FIG. 1

$$Ni^{2+} + 2\ H_2N\text{-}CH_2CH_2\text{-}NH_3 + 4\ CH_2O + 2\ RNH_2$$

POLYMERIC FOOD SPOILAGE SENSOR

CROSS-REFERENCE TO RELATED APPLICATIONS

This application is a national stage application of International Application No. PCT/US01/11701, filed Apr. 9, 2001 which claims the benefit of prior filed U.S. application Ser. No. 60/195,934, filed on Apr. 10, 2000.

BACKGROUND OF THE INVENTION

1. Field of the Invention

The present invention relates to a polymeric sensor having selective binding affinity for an analyte which is indicative of food spoilage. More particularly, this invention is directed to a polymer containing incorporated therein a macrocyclic transition metal complex which selectively binds a biogenic amine, whereupon the polymer undergoes a detectable color change and thereby indicates the extent of food spoilage. Selectivity of the polymer sensor may be enhanced through the process of molecular imprinting.

2. Description of the Related Art

Polymeric sensors are prepared by ionically or covalently attaching an atomic, ionic, or molecular site to a polymer that, upon association with a particular analyte, will exhibit a detectable change in a measurable physical property. Exemplary measurable physical properties include spectroscopic (i.e., electronic absorbance or luminescence), electrochemical, or magnetic properties. The change in the physical property then provides a probe for the presence or absence of the associated analyte that can be measured using appropriate instrumentation or by direct observation. The polymer provides a support matrix that serves to immobilize the sensor sites and provide a localized density of the sensor sites as a means of optimizing detection of the analyte.

Molecular imprinting essentially involves making a polymer cast of a target molecule. The process of making the polymer cast involves dissolving the target molecule to be imprinted in a suitable solvent. Normally, a co-monomer, cross-linking monomer and a polymerization initiator are added to the reaction mixture. Radiation (photochemical or ionizing) or thermal energy is then applied to the reaction mixture to drive the polymerization process, ultimately resulting in the formation of a solid polymer. The resulting polymer may be processed using conventional polymer processing technologies, assuming those processes do not alter the structure of the molecularly imprinted sites. The imprinted molecule is extracted using methods appropriate for dissociating the target molecule from the polymer. Details of target molecule dissociation from the polymer are dependent upon the nature of the chemical interaction between the target molecule and the polymer binding site. The polymer dissociated from the target molecule possesses binding sites optimized for the structural and electronic properties of the target molecule. Mosbach U.S. Pat. No. 5,110,833 describes the preparation of synthetic enzymes and synthetic antibodies by molecular imprinting techniques.

The advantages to polymer sensors, including molecularly imprinted polymer (MIP) sensors, include their high molecular sensitivity, robustness, long storage life without losing their sensitivity, low cost, and ease of production. It is for these reasons that MIPs are being utilized in many industries. Current biomedical applications include drug monitoring devices and implants to monitor glucose levels.

Figure 1:
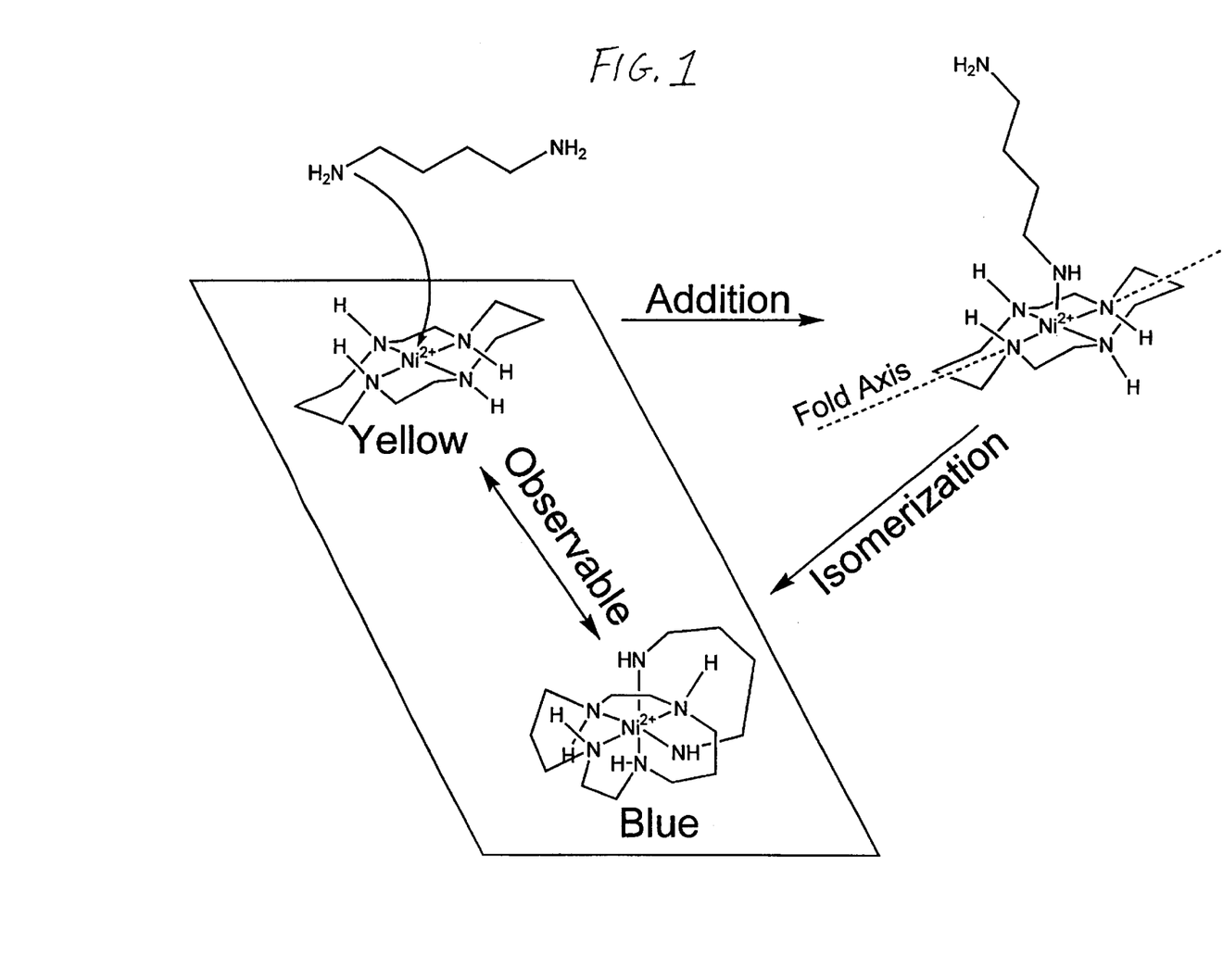
FIG. 1 is a schematic representation of the mechanism for the yellow to blue/violet interconversion upon exposure of a diamine to a macrocyclic Ni(II) complex.

Tetraazacyclotetradecanenickel(II), referred to as Ni(cyclam)$^{2+}$, due to its geometric properties and resulting large ligand field stabilization energy, exists in water predominantly as a square planar, four-coordinate, yellow-colored complex (Connolly, P. J.; Billo, E. J. *Inorg. Chem.* 1987, 26, 3224–3226). Upon addition of ethylene diamine, aqueous solutions of Ni(cyclam)$^{2+}$ turn from yellow to a blue/violet color, the origin of which has been attributed to cis coordination of the diamine to two adjacent coordination sites of the central nickel(II)ion (Billo, E. J. *Inorg. Chem.* 1984 23, 2223–2227). The availability of the cis coordination sites on the nickel(II) ion is made possible by folding of the cyclam ligand, a process that is known to involve isomerization of the nitrogen donor set (Barefield, E. K.; Bianchi, A.; Billo, E. J.; Connolly, P. J.; Paoletti, P.; Summers, J. S.; Van Derveer, D. G. *Inorg. Chem.* 1986, 25, 4197–4202). The change in geometry from four-coordinate in the absence of the diamine to six-coordinate in the presence of the diamine results in a change in the ligand field splitting of the central nickel(II) ion, and the blue/violet color of the product. See FIG. 1.

A Ni(II) complex related to Ni(cyclam)$^{2+}$, 1,8-dimethyl-1,3,6,8,10,13-hexaazacyclotetradecanenickel(II), referred to as Ni(Me$_2$[14]aneN$_6$)$^{2+}$, possesses a 14-membered skeleton structure, although the propylene bridges of cyclam are now replaced with tertiary amines. This compound is known to exist predominantly in the yellow form in aqueous solution and has properties similar to those of Ni(cyclam)$^{2+}$ (Suh, M. P.; Kang, S.-G. *Inorg. Chem.* 1988, 27, 2544–2546). A related compound, with 2-hydroxyethyl groups at the 1 and 8 positions in place of the methyl groups, has recently been found to react with ethylene diamine to yield a cis-hexacoordinate nickel(II) complex (Xiang, H.; Lu, T.-B; Chen, S.; Mao, Z.-W; Feng, X.-L; Yu, K.-B. *Polyhedron* 2001, 20, 313–319).

Meat spoilage occurs as bacteria begin to grow unchecked following respiration and circulation cessation at the time of slaughter. One of the markers of meat spoilage is the decarboxylation of free amino acids on and in the meat by enzymes released by spoilage microorganisms. Two of these products, putrescine and cadaverine, are particularly distinctive in odor, correlate well with surface bacterial counts, and are widely used to evaluate meat freshness both by trained meat inspectors and the individual consumers. Another product, histamine, is of interest due to its apparent ability to potentiate histamine intoxication, a form of food poisoning associated with the consumption of spoiled fish.

Accordingly, there is a need for a robust sensor device which accurately, simply and rapidly detects the presence of biogenic amines in food products.

SUMMARY OF THE INVENTION

The present invention provides a polymeric sensor which exhibits selective binding affinity for biogenic amine and undergoes a detectable change in absorption or emission of electromagnetic radiation upon exposure to biogenic amine. Upon contact with biogenic amine, such as putrescine (1,4-diaminopentane), cadaverine (1,5 diaminopentane) and/or histamine (5-imidazole-ethylamine), the polymer typically undergoes a detectable color change from yellow to blue/violet. The polymer is formed by the steps comprising:

(A) providing a four-coordinate polyazamacrocyclic transition metal complex containing one or more polymerizable moieties;

(B) copolymerizing the transition metal complex of step (A) with monomer and optional crosslinking agent to form a polymer which exhibits selective binding affinity for biogenic amine and undergoes a detectable color change when the target molecule binds thereto.

In another embodiment, in step (A) the four-coordinate polyazamacrocylclic transition metal complex is reacted with a target molecule comprising at least one biogenic amine to provide a reaction product possessing five or six-coordinate geometry. This reaction product, monomer and optional crosslinking agent are then copolymerized using conventional techniques to produce a polymer. Thereafter, the target molecule is removed from the polymer to provide a molecularly imprinted polymer which exhibits selective binding affinity for the target molecule and undergoes a detectable color change when the target molecule binds thereto.

The color change may be in the UV, visible or near infrared region or some combination thereof and will occur to an extent dependent upon the concentration of biogenic amine to which the polymer is exposed. For food spoilage applications, significant color change will take place when the polymer is exposed to approximately 20 ppm or more of biogenic amine.

The polymer of the invention can be employed by itself as as a sensor to monitor the presence of biogenic amine in food products, particularly meats and fish, on a spot or continuous basis. For example, the polymer can be easily incorporated into common food containers to provide an easily detectable indication of probable spoilage of the food contents within the container.

This invention provides a sensor for detecting the presence of biogenic amine in, on or in association with a food which comprises the polymer and a support structure having a surface, said polymer being attached to said support structure as a coating thereon. In one embodiment the support structure is a plastic sheet, film or tray which is utilized in the packaging of food products. In another embodiment, the support structure is an optical fiber.

The invention also provides a method for detecting food spoilage, comprising:

exposing the polymer of this invention to an environment containing food, e.g., meat or fish, such that fluids (vapors and/or liquids) from the food come in contact with the polymeric sensor, and detecting any change in color by the polymer, said detected change being indicative of the presence of biogenic amine in, on or in association with said food.

Additional aspects, embodiments and advantages of the present invention will be set forth, in part, in the description that follows, or may be learned from practicing or using the present invention. The objects and advantages may be realized and attained by means of the features and combinations particularly pointed out throughout this description and the appended claims. It is to be understood that the foregoing general description and the following detailed description are exemplary and explanatory only and are not to be viewed as being restrictive of the invention as claimed.

DESCRIPTION OF THE PREFERRED EMBODIMENTS

References cited throughout this written description are incorporated herein in their entirety to more fully describe the state of the art to which they pertain.

As used herein, the phrase "polymeric sensor" refers to the polymer disclosed herein as well as the polymer in combination with one or more substrates or devices. As used herein the phrase "molecularly imprinted polymer" refers to a molecular mold-like structure that has preorganized interactive moieties complementing the shape and electronic properties of a target molecule comprising a biogenic amine, such as putrescine, cadaverine and histamine. The interactive moieties are polyazamacrocyclic transition metal complexes possessing a geometrical organization which imparts selective binding characteristics for the biogenic amine. The term "selective binding" is intended to refer to preferential and reversible binding exhibited by the polymeric sensor herein for spoilage indicating biogenic amine compared to molecules having similar structural features and that are present in significant quantities in and on food products, e.g., spermine and spermidine biogenic amines that are present in similar concentrations in both fresh and spoiled meat. Selective binding includes both affinity and specificity of the polymer for spoilage indicating biogenic amine.

The origins of molecularly imprinted molecules trace back to the notion of Linus Pauling that the body assembled a new protein complement (i.e., an antibody) by using the foreign intruder as a template. Although it was later determined that this is not how antibodies are selected in vivo, this template concept stimulated significant thought and research. Molecular imprinting creates specific recognition sites in materials, such as polymeric organic materials. Known molecular imprinting techniques involve crosslinking materials in the presence of a functional monomer or mixture of monomers. The template molecule interacts with a complementary portion of a functional monomer or monomers by maximizingcovalent ionic, ion-dipole, hydrogen bonding, dipole-dipole, induced dipole or instantaneous dipole-induced dipole (i.e., London dispersion) attractive interactions, and minimizing coulombic and steric repulsive interactions. In such a way, molecular level recognition sites for the template molecule can be provided in the substrate material. The template molecule is then removed from the substrate to leave a "cavity" or recognition site. Linus Pauling reasoned that shape specificity was obtained by using a target antigen to arrange the complementary shape of an antibody. Thus, a nonspecific molecule can be shaped to the contours of a specific target, and when the target is removed, the shape is maintained to give the antibody a propensity to rebind the antigen. This process is known as "molecular imprinting" or "templating."

Methods for preparing MIPs are described in U.S. Pat. Nos. 4,406,792, 4,415,655, 4,532,232, 4,935,365, 4,960,762, 5,015,576, 5,110,883, 5,208,155, 5,310,648, 5,321,102, 5,372,719, 5,786,428, 6,063,637, the contents of which are incorporated by reference herein.

An MIP in accordance with the principles of the present invention can be prepared by the steps which comprise:

(A) providing the reaction product of (i) a four-coordinate polyazamacrocyclic transition metal complex containing one or more polymerizable moieties and (ii) a target molecule comprising biogenic amine selected from the group consisting of cadaverine, putrescine and histamine, said reaction product possessing a six-coordinate geometry;

(B) copolymerizing the reaction product of step (A) with monomer and crosslinking agent to form a polymer; and (C) removing the target molecule from the polymer to provide a molecularly imprinted polymer which exhibits selective binding affmity for the target molecule and undergoes a detectable color change when the target molecule binds thereto. The polymerization reaction mixture for the preparation of the MIP therefore constitutes the reaction product of step (A), one or more polymerizable monomers, one or more (optional) crosslinking agents to impart a sufficiently rigid structure to the polymer end-product (where desired), solvent, and a polymerization initiator. More than one monomer and/or crosslinking agent can be used in the polymerization method.

The polyazamacrocyclic transition metal complex corresponds to the formula:

wherein M is a transition metal ion;

$n_1$, $n_2$, $n_3$, $n_4$ can be the same or different and can be 0 or 1;

$D_1$, $D_2$, $D_3$, and $D_4$ can be the same or different and can be C, N, O, S, or P;

$B_{1a}$, $B_{1b}$, $B_{2a}$, $B_{2b}$, $B_{3a}$, $B_{3b}$, $B_{4a}$, and $B_{4b}$ can be the same or different and can be H, F, $CH_3$, alcohol, allyl, amine, styrene, methacrylate, acrylate, vinyl, vinyl ether, vinyl acetate, trialkoxysilane, dialkoxycholorosilane and epoxy;

$X_1$, $X_2$, $X_3$, and $X_4$ can be the same or different and can be N, C, H, or B;

$A_{1a}$, $A_{1b}$, $A_{2a}$, $A_{2b}$, $A_{3a}$, $A_{3b}$, $A_{4a}$, and $A_{4b}$ can be the same or different and can be H, F, $NH_3$, $NO_2$, $CO_2^-$, $CO_2H$, $CO_2R$, alcohol, allyl, styrene, methacrylate, acrylate, vinyl, vinyl ether, vinyl acetate, trialkoxysilane, dialkoxycholorosilane and epoxy;

$Y_{1a}$, $Y_{1b}$, $Y_{2a}$, $Y_{2b}$, $Y_{3a}$, $Y_{3b}$, $Y_{4a}$, and $Y_{4b}$ may be the same or different, and can be C or O; and, $C_{1a}$, $C_{1b}$, $C_{2a}$, $C_{2b}$, $C_{3a}$, $C_{3b}$, $C_{4a}$, $C_{4b}$, $C_{5a}$, $C_{5b}$, $C_{6a}$, $C_{6b}$, $C_{7a}$, $C_{7b}$, $C_{8a}$, and $C_{8b}$ can be the same or different and can be H, F, $NH_3$, $NO_2$, $CO_2^-$, $CO_2H$, $CO_2R$, alcohol, allyl, styrene, methacrylate, acrylate, vinyl, vinyl ether, vinyl acetate, trialkoxysilane, dialkoxycholorosilane and epoxy.

The macrocycle structure may be fully saturated or unsaturated to varying degrees, provided the degree of unsaturation does not interfere with folding of the macrocycle to a sufficient degree that adjacent coordination sites become no longer available.

Preferred are macrocyclic compounds corresponding to the general formula above wherein M is nickel(II), $D_1$, $D_2$, $D_3$, and $D_4$ are N, $Y_{1a}$, $Y_{1b}$, $Y_{2a}$, $Y_{2b}$, $Y_{3a}$, $Y_{3b}$, $Y_{4a}$, and $Y_{4b}$ are C, $n_1$ and $n_3$ are 1, $n_2$ and $n_4$ are 0, $X_1$ and $X_3$ are N, $A_{1a}$ and $A_{3a}$ are styrene, vinyl, amine or carboxyl, and $A_{1a}$ and $A_{3a}$ are electron lone pairs.

Figure 2:
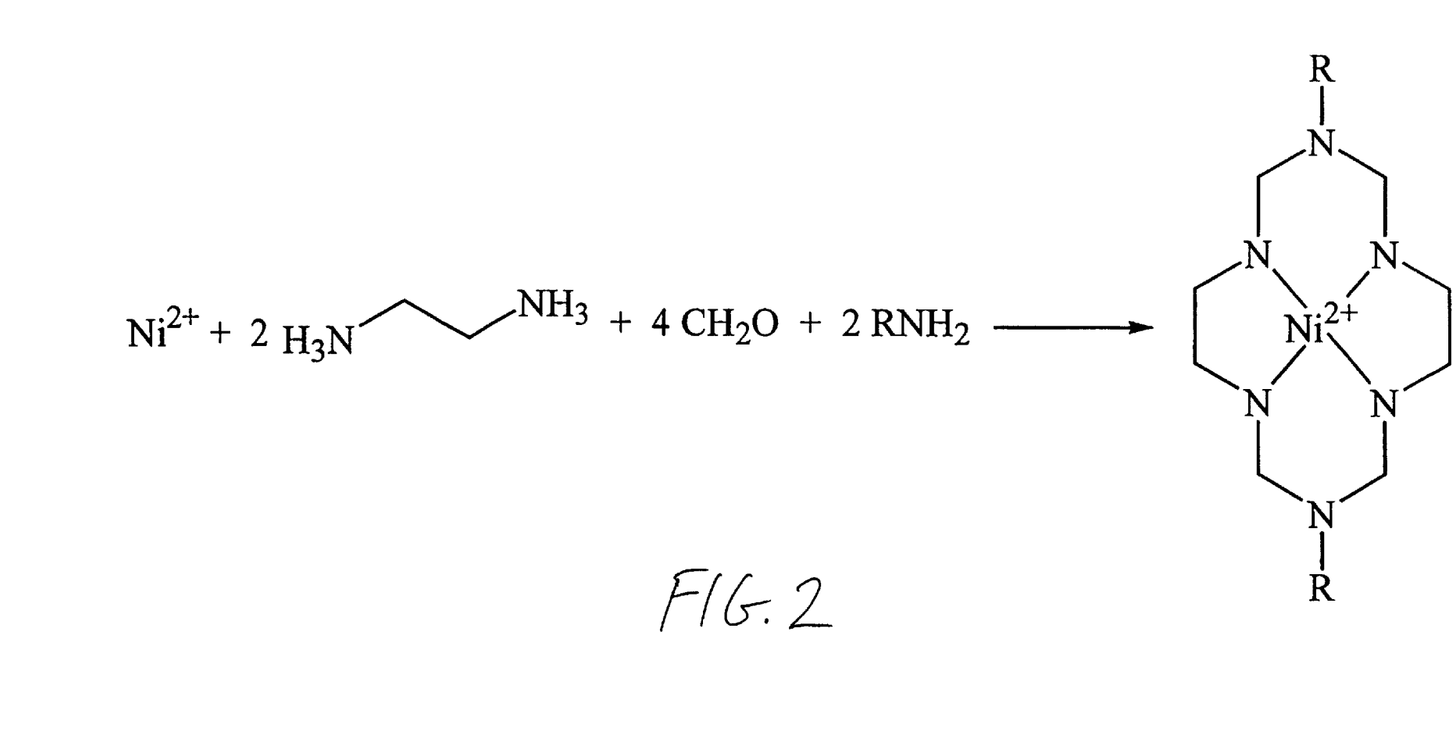
FIG. 2 is a chemical reaction scheme that can be employed to synthesize a polymerizable four-coordinate, yellow colored polyazamacrocyclic transition metal complex.

Methods for synthesizing polyazamacrocyclic compounds are known. See, e.g., Suh, M. P.; Kang, S.-G. *Inorg. Chem.* 1988, 27, 2544–2546; Hay, R. W.; Crayston, J. A.; Cromie, T. J.; Lightfoot, P.; de Alwis, D. C. L. *Polyhedron* 1997, 16,3557–3563; Fabbrizzi, L.; Licchelli, M.; Poggi, A.; Vassalli, O.; Ungaretti, L.; Sardone, N. *Inorg Chim. Acta* 1996, 246, 379–385; Gobi, K. V.; Tokunda, K.; Ohsaka, T. *Electrochimica Acta* 1998, 43, 1013–1022; Kang, S.-G.; Ryu, K.; Jung, S.-K.; Kim, J. *Inorg. Chim. Acta* 1999, 293, 140–146; Shakir, M.; Mohamed, A. K.; Varkey, S. P.; Nasman, O. S. M.; Siddiqi, Z. A. *Polyhedron* 1995, 14, 1277–1282, and U.S. Pat. Nos. 4,001,212 and 5,587,451, the contents of which are incorporated by reference herein. The synthesis of a preferred macrocycle, i.e., the 1,8-disubstituted-hexaazatetradecane nickel(II) complex, is depicted in FIG. 2. As shown therein, stoichiometric amounts of solvated nickel(II) is reacted with two equivalents of ethylene diamine, four equivalents of formaldehyde, and two equivalents of a primary amine, $RNH_2$ wherein R is a polymerizable functional group. The polymerizable functional group may take a variety of forms although examples may be selected from the group consisting of styrene, methacrylate, acrylate, vinyl, vinyl, ether, vinyl acetate, amine, carboxyl, hydroxyl, trialkoxysilane, dialkoxysilane and epoxy, to form the derivatized nickel(II) complex of hexaazatetradecane which is substituted by polymerizable R groups at the 1 and 8 positions on the polyamine macrocycle. It will be apparent to those skilled in the art that alternate pathways to synthesizing the product depicted in FIG. 2 are possible.

A wide variety of monomers may be used for synthesizing the polymer sensor in accordance with the principles of the present invention. Preferred monomers include methyl methacrylate, and styrene. Examples of other suitable monomers include all molecules capable of undergoing addition or condensation polymerization. This class includes, but is not limited to, those described in the references cited in this written description and incorporated by reference herein. Further suitable non-limiting examples of monomers that can be used for preparing a polymer of the present invention include methylmethacrylate, other alkyl methacrylates, alkylacrylates, ally or aryl acrylates and methacrylates, cyanoacrylate, styrene, .alpha.-methyl styrene, vinyl esters, including vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)-.alpha.-acryloxy-.beta., .beta.'-dimethyl-g-butyrolactone; N-acryloxy succinimide N-acryloxytri.s(hydroxymethyl)aminomethane; N-acryloly chloride; N-acryloyl pyrrolidinone; N-acryloyl-tris(hydroxymethyl)amino methane; 2-amino ethyl methacrylate; N-(3-aminopropyl)methacrylamide; (o, m, or p)-amino-styrene; t-amyl methacrylate; 2-(1-aziridinyl)ethyl methacrylate; 2,2'-azobis-(2-amidinopropane); 2,2'-azobisisobutyronitrile; 4,4'-azobis-(4-cyanovaleric acid); 1,1'-azobis-(cyclohexanecarbonitrile); 2,2'-azobis-(2,4- dimethylvaleronitrile); 4-benzyloxy-3-methoxystyrene; 2-bromoacrylic acid; 4-bromo-1-butene; 3-bromo-3,3-difluoropropane; 6-bromo-1-hexene; 3-bromo-2-methacrylonitrile; 2-(bromomethyl)acrylic acid; 8-bromo-1-octene; 5-bromo-1-pentene; cis-1-bromo-1-propene; .beta.-bromostyrene; p-bromostyrene; bromotrifluoro ethylene; (±)-3-buten-2-ol; 1,3-butadiene; 1,3-butadiene-1,4-dicarboxylic acid 3-butenal diethyl acetal; 1-butene; 3-buten-2-ol; 3-butenyl chloroformate; 2-butylacrolein; N-t-butylacrylamide; butyl acrylate; butyl methacrylate; (o,m,p)-bromostyrene; t-butyl acrylate; (R)-carvone; (S)-carvone; (−)-carvyl acetate; cis 3-chloroacrylic acid; 2-chloroacrylonitrile; 2-chloroethyl vinyl ether; 2-chloromethyl-3-trimethylsilyl-1-propene; 3-chloro-1-butene; 3-chloro-2-chloromethyl-1-propene; 3-chloro-2-methyl propene; 2,2-bis(4-chlorophenyl)-1,1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy) ethylene; 2,3-dichloro-1-propene; 2,6-dichlorostyrene; 1,3-dichloropropene; 2,4-diethyl-2,6-heptadienal; 1,9-decadiene; 1-decene; 1,2-dibromoethylene; 1,1-dichloro-2,2-difluoroethylene; 1,1-dichloropropene; 2,6-difluorostyrene; dihydrocarveol; (±)-dihydrocarvone; (−)-dihydrocarvyl acetate; 3,3-dimethylacrylaldehyde; N,N'-dimethylacrylamide; 3,3-dimethylacrylic acid; 3,3-dimethylacryloyl chloride; 2,3-dimethyl-1-butene; 3,3dimethyl-1-butene; 2-dimethyl aminoethyl methacrylate; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4-dimethylstyrene; 2,5-dimethylstryene; 3,4-dimethylstryene; divinyl benzene; 1,3-divinyltetramethyl disiloxane; 8,13-divinyl-3,7,12,17-tetramethyl-21H,23H-porphine; 8,13-divinyl-3,7,12,17-tetramethyl-21H,23H-propionic acid; 8,13-divinyl-3,7,12,17-tetramethyl-21H,23H-propionic acid disodium salt; 3,9-divinyl-2,4,8,10-tetraoraspiro[5,5]undecane; divinyl tin dichloride; 1-dodecene; 3,4-epoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl-2-(hydroxymethyl)-1,3-propanediol trimethacrylate; ethyl methacrylate; ethyl vinyl ether; ethyl vinyl ketone; ethyl vinyl sulfone; (1-ethylvinyl)tributyl tin; m-fluorostyrene; o-fluorostyrene; p-fluorostyrene; glycol methacrylate (hydroxyethyl methacrylate); GA GMA; 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4-diol; 1,4-hexadiene; 1,5-hexadien-3-ol; 1,3,5-hexatriene; 5-hexen-1,2-diol; 5-hexen-1-ol; hydroxypropyl acrylate; 3-hydroxy-3,7,11-trimethyl-1,6,10-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene isocyanate; isopulegol; itaconic acid; itaconalyl chloride; lead (II) acrylate; (±)-:linalool; linalyl acetate; p-mentha-1,8-diene; p-mentha-6,8-dien-2-ol; methyleneamino acetonitrile; methacrolein; [3-(methacryloylamino)-propyl]trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl)trimethoxy silane; 2-(methacryloxy) ethyl trimethyl ammonium methylsulfate; 2-methoxy propene (isopropenyl methyl ether); methyl-2-(bromomethyl) acrylate; 5-methyl-5-hexen-2-one; methyl methacrylate; N,N'-methylene bisacrylamide; 2-methylene glutaronitrile; 2-methylene-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-1-pentene; .alpha.-methyl styrene; t-a-methylstyrene; t-.beta.-methylstyrene; 3-methylstyrene; methyl vinyl ether; methyl vinyl ketone; methyl-2-vinyloxirane; 4-methylstyrene; methyl vinyl sulfonee; 4-methyl-5-vinylthiazole; myrcene; t-.beta.-nitrostyrene; 3-nitrostyrene; 1-nonadecene; 1,8-nonadiene; 1-octadecene; 1,7-octadiene; 7-octene-1,2-diol; 1-octene; 1-octen-3-ol; 1-pentadecene; 1-pentene; 1-penten-3-ol; t-2,4-pentenoic acid; 1,3-pentadiene; 1,4-pentadiene; 1,4-pentadien-3-ol; 4-penten-1-ol; 4-penten-2-ol; 4-phenyl-1-butene; phenyl vinyl sulfide; phenyl vinyl sulfonate; 2-propene-1-sulfonic acid sodium salt; phenyl vinyl sulfoxide; 1-phenyl-1-(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachioroethylene; tetracyano ethylene; tetramethyldivinyl siloxane; trans 3-chioroacrylic acid; 2-trifluoromethyl propene; 2-(trifluoromethyl)propenoic acid; 2,4,4'-trimethyl-1-pentene; 3,5-bis(trifluoromethyl)styrene; 2,3-bis(trimethylsiloxy)-1,3-butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-(p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotanoate; vinyl cyclohexane; 4-vinyl-1-cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; 1-vinyl imidizole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbornene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfone (divinylsulfone); vinyl sulfonic acid sodium salt; o-vinyl toluene; p-vinyl toluene; vinyl triacetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl triethyl nonylether; vinyl triethyl silane; vinyl triphenyphosphonium bromide (triphenyl vinyl phosphonium bromide); vinyl tris-(2-methoxyethoxy)silane; vinyl 2-valerate and the like.

Acrylate-terminated or otherwise unsaturated urethanes, carbonates, and epoxies can also be used in the polymer. An example of an unsaturated carbonate is allyl diglycol carbonate (CR-39). Unsaturated epoxies include, but are not limited to, glycidyl acrylate, glycidyl methacrylate, allyl glycidyl ether, and 1,2-epoxy-3-allyl propane.

Crosslinking agents, i.e., monomers that possess two or more polymerizable functional groups, that impart rigidity to the polymer are known to those skilled in the art, and include di-, tri- and tetrafunctional acrylates or methacrylates, divinylbenzene (DVB), alkylene glycol and polyalkylene glycol diacrylates and methacrylates, including ethylene glycol dimethacrylate (EGDMA) and ethylene glycol diacrylate, vinyl or allyl acrylates or methacrylates, divinylbenzene, diallyldiglycol dicarbonate, diallyl maleate, diallyl fumarate, diallyl itaconate, vinyl esters such as divinyl oxalate, divinyl malonate, diallyl succinate, triallyl isocyanurate, the dimethacrylates or diacrylates of bis-phenol A or ethoxylated bis-phenol A, methylene or polymethylene bisacrylamide or bismethacrylamide, including hexamethylene bisacrylamide or hexamethylene bismethacrylamide, di(alkene) tertiary amines, trimethylol propane triacrylate, pentaerythritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methy:L-2-isocyanatoethyl methacrylate, 1,1-dimethyl-2-isocyanaotoethyl acrylate, tetraethylene glycol diacrylate, tetraethylene glycol dimethacrylate, triethylene glycol diacrylate, triethylene glycol dimethacrylate, hexanediol dimethacrylate, hexanediol diacrylate, and the like.

While free radical polymerization is preferred, monomers can also be selected that are polymerized cationically or anionically. Polymerization conditions should be selected that do not adversely affect the analyte binding site. Any photochemical, radiation chemical, or thermal free radical initiator known to those skilled in the art for free radical polymerization can be used to initiate this method. Examples of UV and thermal initiators include benzoyl peroxide, acetyl peroxide, lauryl peroxide, azobisisobutyronitrile (AIBN), t-butyl peracetate, cumyl peroxide, t-butyl peroxide, t-butyl hydroperoxide, bis(isopropyl)peroxydicarbonate, benzoin methyl ether, 2,2'-azobis(2,4-dimethylvaleronitrile), tertiarybutyl peroctoate, phthalic peroxide, diethoxyacetophenone, and tertiarybutyl peroxypivalate, diethoxyacetophenone, 1-hydroxycyclohexyl phenyl ketone, 2,2-dimethyoxy-2-phenyl-acetophenone, and phenothiazine, and diisopropylxanthogen disulfide.

The choice of monomer and cross-linking agent will be dictated by the chemical (hydrophilicity, chemical stability, degree of cross-linking, ability to graft to other surfaces, interactions with other molecules, etc.) and physical (porosity, morphology, mechanical stability, etc.) properties desired for the polymer. The procedures and conditions which are used to copolymerize the polyazamacrocyclic transition metal complex, monomers and cross-linking agent are conventional. The amounts of polyazamacrocyclic compound, monomer and crosslinking agents should be chosen to provide a crosslinked polymer exhibiting the desired structural integrity, porosity and hydrophilicity. The amounts can vary broadly, depending on the specific nature/reactivities of the polyazazmacrocyclic compound, monomer and crosslinking agent chosen as well as the specific sensor application and environment in which the polymer/sensor will be ultimately employed. The relative amounts of each reactant can be varied to achieve desired concentrations of polyazamacrocyclic transition metal complexes in the polymer support structure. Typically, the amount of polyazamacrocyclic compound will be on the order of about 0.5 to about 1.5 mole percent of monomer. The solvent, temperature, and means of polymerization can be varied in order to obtain polymeric materials of optimal physical or chemical features, for example, porosity, stability, and hydrophilicity. The solvent will also be chosen based on its ability to solubilize all the various components of the reaction mixture.

Polymerizations are generally conducted in bulk solution by the free-radical method. Similar methodology can be applied to surface grafting and particle coating with the polymer, as described in "Surface Grafting of Functional Polymers to Macroporous Poly Trimethylolpropane Trimethacrylate," P. K. Dhal, S. Vidyasarikar and F. H. Arnold, Chemistry of Materials 7, 154–162 (1995) and "Molecularly-Imprinted Polymers on Silica: Selective Supports for High Performance Ligand-Exchange Chromatography," S. D. Plunkett and F. H. Arnold, J. Chromatogr. A 708, 19–29 (1995).

For bulk polymerization, typically about 0.5 to about 1.5 mol percent of the polymerizable polyazamacrocyclic compound, about 90 to about 99 mol percent monomer and about 1.0 to about 10 mol percent cross-linker, and about 1 mol percent of a free radical initiator such as 2,2'-azobis(2-methylpropionamide) dihydrochloride are dissolved in an aqueous/organic two-phase solvent. The reaction mixture is placed under an inert atmosphere and heated at about 60.0° C. for about 2 to about 72 hours.

Polymerizations can be carried out by a sol-gel process when an alkoxysilane-type of polymerizable compound is used. In this case, the alkoxysilane substituted macrocyclic metal ion complex monomer is hydrolyzed with, for example, tetramethoxysilane, tetraethoxysilane, or poly (glyceryl silicate) in a suitable solvent (see for example, Louloudi, M.; Deligiannakis, Y.; Hadjiliadis, N. Inorg. Chem. 1998, 37, 6847–6851; Katz, A.; Davis, M. E. Nature 2000, 403, 286; Kloster, G. M.; Taylor, C. M.; Watton, S. P. Inorg. Chem. 1999, 38, 3954–3955. The sol-gel condensation can be conducted in acidic or basic conditions using procedures well known to those practiced in the art.

The morphology and selectivity of the polymer for binding the target molecule may be improved by altering the solvent, polymerization temperature, and choice of crosslinking agent, as described in Sellergren, B., Shea, K. J., "Influence Of Polymer Morphology On The Ability Of Imprinted Network Polymers To Resolve Enantiomers," J. Chromatogr. A 1993, 635:31–40.

Figure 3:
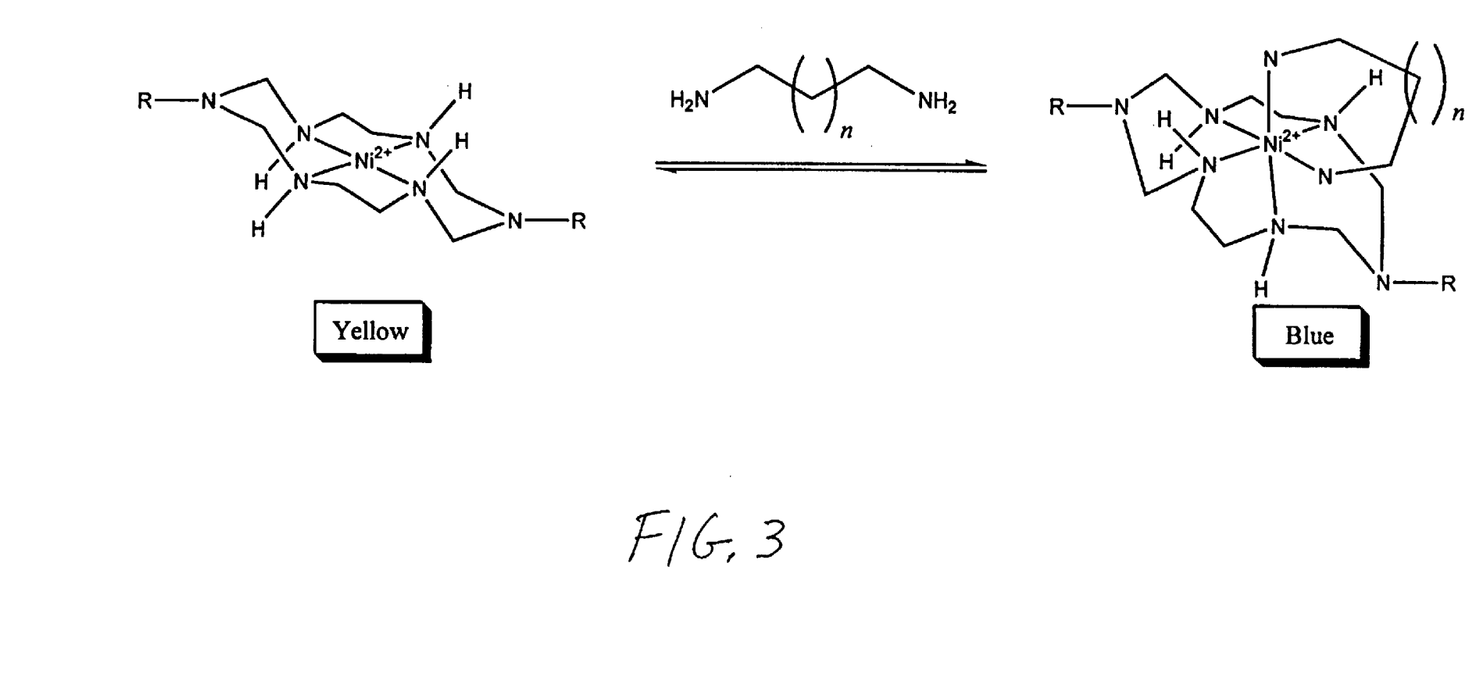
FIG. 3 depicts a chemical equilibrium reaction between a polymerizable four-coordinate, yellow-colored polyazamacrocyclic transition metal complex and diamine to produce a six-coordinate, blue-colored reaction product.

Removal of the target molecule leaves a macroporous polymer with complementary molecular cavities which include polyazamacrocyclic transition metal complexes that have specific binding affinity for biogenic amine. See FIG. 3. The target molecule comprising biogenic amine may be dissociated from the metal ion complex binding site within the polymer by extraction into acidified water.

The polymer of the invention can be prepared in a wide variety of forms ranging from powders to beads to macro structures such as films, plates, rods, membranes or coatings or other materials. A wide range of sensors can be produced from the polymer of the invention, and the type of sensor will depend on the conditions of use(e.g., spot monitoring, continuous monitoring, process monitoring, whether used during processing, packaging or storage of food, whether used at point of sale or at home, etc.).

The polymer can be easily incorporated into common food containers to provide a quick and easily detectable indication of probable deterioration of the food contents within the container.

Therefore, this invention provides a sensor for detecting the presence of biogenic amines in a food which comprises the polymer. In one embodiment the sensor is a self supporting film placed under the (transparent) packaging material. In another embodiment, the sensor serves as, or is a portion of, the packaging material. The sensor may include a support structure having a surface, said polymer being attached to said support structure as a coating thereon. In one embodiment the support structure is a plastic sheet, film or tray which is utilized in the packaging of food products.

The invention also provides a method for detecting food spoilage, comprising:

exposing the polymer of this invention to an environment containing meat or fish such that fluids, i.e., vapors and/or liquids, from the meat or fish come in contact with the polymer, and detecting any change in color by the polymer, said detected change being indicative of the presence of biogenic amine in, on or in association with said meat or fish.

In one embodiment, the sensor comprises a simple colorimetric indicator, e.g., stick or strip, in which exposure to biogenic amine would result in a visual color change from yellow to blue/violet. The scope of the invention is not limited to any one particular type of indicator. For example, U.S. Pat. Nos. 2,485,566, 3,067,015, 4,003,709, 4,285,697, 5,306,466, 5,439,648 and 5,653,941, the contents of which are incorporated by reference herein, all disclose food spoilage indicators for use in packages which may find application in the present invention.

In another embodiment, the change in color of the polymer is detected by a spectroscopic method, such as measurement of the transmittance and/or reflectance spectra, suitably employing fiberoptics and or microelectronic devices.

The change may be detected by removing a sample of fluid from the environment in which biogenic amine may be present for detection, for example, spectroscopically. Preferably, the monitoring is carried out in situ, for example, by providing the polymer of the invention on the packaging or adjacent the foodstuff to be monitored, suitably by using a fiber light guide to and from the polymer to enable detection by remote measurement, or by a small electronic device Alternatively, an optical fiber may be itself coated with the polymer and, if necessary, the coating sealed with a further coating layer of transparent or translucent polymeric material. Such an optical fiber may, for example, be mounted within a storage refrigerator to enable detection in situ of a color change resulting from spoilage of stored foodstuffs. It is envisioned therefore that optical fibers or microelectronic devices, or a network thereof, may be used in connection with commercial refrigeration plants, to enable continuous monitoring of the contents of the plants.

Therefore, according to a further aspect of the invention, there is provided an apparatus suitable for use in the monitoring method as described above comprising a source of electromagnetic radiation of wavelength covering the region in which the change is to be detected, means for transmitting such radiation to biogenic amine, means for exposing the biogenic amine to the environment to be monitored and means for detecting a change in absorption or reflection of the electro-magnetic radiation due to the association of a biogenic amine with the polymer sensor. Such an apparatus is disclosed in U.S. Pat. No. 5,663,072, incorporated by reference herein.

As can be appreciated by the skilled artisan, the preferred synthetic schemes and embodiments described above and in the Examples below are not intended to comprise a comprehensive list of all means by which the polymer sensor described and claimed herein may be synthesized. It will be understood that the specified materials and conditions are important in practicing the invention but that unspecified materials and conditions are not excluded so long as they do not prevent the benefits of the invention from being realized. Other suitable methods and starting materials will be evident to those having skill in the art. Additionally, the various synthetic steps described throughout this written description may be performed in an alternate sequence or order to obtain the present invention.

EXAMPLES

Example 1

Synthesis of chloride salt 1,8-diallyl-1,3,6,8,10,13-hexazacyclotetradecane Nickel (II)

The complex 1,8-diallyl-1,3,6,8,10,13-hexaazacyclotetradecane nickel(II) chloride was prepared by dissolving 11.55 g $NiCl_2 \cdot xH_2O$ (Aldrich 99.95%, used as received, ~50 mmol) in 50 mL methanol (B&J Brand), to give a dark green solution. The solution was transferred to a 250 mL, 2-neck, round bottom flask and stirred magnetically. To this solution was added 6.8 mL of clear colorless ethylene diamine (Aldrich 99+%, 100 mmol), to give a deep purple solution. To this solution was added 20 mL formaldehyde (Aldrich 37 wt. %, aq, 270 mmol), resulting in a color change to a deep aqua blue. Lastly, 7.5 mL allylamine (Aldrich 99+%, 100 mmol) was added with no apparent change in color. The methanol solution was brought to reflux for 15–24 hours. To the reaction mixture was added 1 mL concentrated HCl with stirring and the suspension was allowed to stand in the refrigerator for 5 hours. The precipitate formed was collected by vacuum filtration on a fine frit to yield a violet/green sticky solid. The crude product was recrystallized from methanol/diethyl ether. The violet crystalline product was collected on a fine frit by vacuum filtration, which was then washed with 3, 15 mL portions of methanol/diethyl ether (1:1) followed with 2, 10 mL volumes of diethyl ether. Yield 1.21 g or 6% relative to 48 mmol $NiCl_2$.

Example 2

Preparation of Polymer

Step (A)

The complex $[NiL(en)](ClO_4)_2$, where L is the 1,8-diallyl-1,3,6,8,10,13-hexaazacyclotetradecane of Example 1 and "en" is ethylene diamine, was prepared by reacting 0.41 g 1,8-diallyl-1,3,6,8,10,13-hexaazacyclotetradecanenickel (II) chloride (1 mmol) with 1 mL ethylene diamine (Aldrich 99+%, 15 mmol) in 250 mL deionized water with magnetic stirring under ambient atmosphere and temperature. The solution turned from yellow to violet over ~2 hours. To the violet solution was added aqueous sodium perchlorate (Alfa Aesar ACS Reagent 98–102% anhydrous, 0.1 mol dissolved in ~25 mL deionized water). Precipitation of the violet crystalline product began 2 to 5 minutes after addition of the aqueous sodium perchlorate. The suspension was left overnight before vacuum filtering through a fine frit to collect the violet crystalline solid. The product was washed with 3, 7 mL volumes of diethyl ether to yield a fine violet powder. Yield 0.47 g (77%).

Step (B)

Copolymerization of $[NiL(en)](ClO_4)_2$ of Step(A) above with methyl methacrylate and ethylene glycol dimethacrylate has achieved using varying the ratios of the individual reagents. One polymer sample was prepared by dissolving ca. 50 mg ($8.3 \times 10^{-5}$ mol) $[NiL(en)](ClO_4)_2$ in a two phase system composed of 1.0 mL methyl methacrylate (Aldrich 99% washed with 3, 10 mL volumes of 0.5% NaOH followed by 5, 20 mL volumes of deionized water, pH of the final aqueous layer was neutral. The methyl methacrylate layer was used in its water-saturated state), 0.25 mL ethylene glycol dimethacrylate (Aldrich 98%, washed similarly as described for methyl methacrylate), 25 mg 2,2'-azobis(2-methylpropionamide) dihydrochloride (Aldrich 97%), 1.25 mL 0.5% aq. NaOH, and 1.0 mL acetonitrile (B&J Brand). The two phase system was transferred to a vial, capped with a screw cap with a PTFE lined septum, and purged by bubbling with a dry nitrogen flow for ~3 min. The vial was then placed in a 60.0° C. oven and allowed to stand for 5 days. A solid polymer disk is obtained by sacrificing the vial, rinsing the polymer solid with water, and grinding/polishing to remove a whitish solid. The resulting solid appears as a homogeneous, transparent yellow solid.

What is claimed is:

1. A polymer comprising the reaction product of:
   a polyazamacrocylic transition metal complex possessing one or more polymerizable groups;
   monomer; and
   optional crosslinking agent,
   wherein said polymer undergoes a detectable color change upon exposure to a biogenic amine.

2. The polymer of claim 1 wherein the polyazamacrocyclic transition metal complex corresponds to the general formula:

wherein
   M is a transition metal ion;
   $n_1$, $n_2$, $n_3$, $n_4$ can be the same or different and can be 0 or 1;
   $D_1$, $D_2$, $D_3$, and $D_4$ can be the same or different and can be C, N, O, S, or P;
   $B_{1a}$, $B_{1b}$, $B_{2a}$, $B_{2b}$, $B_{3a}$, $B_{3b}$, $B_{4a}$, and $B_{4b}$ can be the same or different and can be H, F, $CH_3$, alcohol, allyl, amine, styrene, methacrylate, acrylate, vinyl, vinyl ether, vinyl acetate, trialkoxysilane, dialkoxycholorosilane and epoxy;
   $X_1$, $X_2$, $X_3$, and $X_4$ can be the same or different and can be N, C, H, or B;
   $A_{1a}$, $A_{1b}$, $A_{2a}$, $A_{2b}$, $A_{3a}$, $A_{3b}$, $A_{4a}$, and $A_{4b}$ can be the same or different and can be H, F, $NH_3$, $NO_2$, $CO_2^-$, $CO_2H$, $CO_2R$, alcohol, allyl, styrene, methacrylate, acrylate, vinyl, vinyl ether, vinyl acetate, trialkoxysilane, dialkoxycholorosilane and epoxy;
   $Y_{1a}$, $Y_{1b}$, $Y_{2a}$, $Y_{2b}$, $Y_{3a}$, $Y_{3b}$, $Y_{4a}$, and $Y_{4b}$ may be the same or different, and can be C or O; and,
   $C_{1a}$, $C_{1b}$, $C_{2a}$, $C_{2b}$, $C_{3a}$, $C_{3b}$, $C_{4a}$, $C_{4b}$, $C_{5a}$, $C_{5b}$, $C_{6a}$, $C_{6b}$, $C_{7a}$, $C_{7b}$, $C_{8a}$, and $C_{8b}$ can be the same or different and can be H, F, $NH_3$, $NO_2$, $CO_2^-$, $CO_2H$, $CO_2R$, alcohol, allyl, styrene, methacrylate, acrylate, vinyl, vinyl ether, vinyl acetate, trialkoxysilane, dialkoxycholorosilane and epoxy.

3. The polymer of claim 2 wherein M is nickel(II), $D_1$, $D_2$, $D_3$, and $D_4$ are N, $Y_{1a}$, $Y_{1b}$, $Y_{2a}$, $Y_{2b}$, $Y_{3a}$, $Y_{3b}$, $Y_{4a}$, and $Y_{4b}$ are C, $n_1$ and $n_3$ are 1, $n_2$ and $n_4$ are 0, $X_1$ and $X_3$ are N, $A_{1a}$ and $A_{3a}$ are styrene, vinyl, amine or carboxyl, and $A_{1a}$ and $A_{3a}$ are electron lone pairs.

4. The polymer of claim 1 wherein the biogenic amine is selected from the group consisting of cadaverine, putrescine and histamine.

5. A food container comprising the polymer of claim 1.

6. A molecularly imprinted polymer formed by the steps of:
   (A) providing the reaction product of (i) a four-coordinate polyazamacrocyclic transition metal complex containing two or more polymerizable moieties and (ii) a target molecule comprising biogenic amine, said reaction product possessing a six-coordinate geometry;
   (B) copolymerizing the reaction product of step (A) with monomer and crosslinking agent to form a polymer; and
   (C) removing the target molecule from the polymer to provide a molecularly imprinted polymer which selectively binds to the target molecule and undergoes a detectable color change when the target molecule binds thereto.

7. The polymer of claim 6 wherein the polyazamacrocylic transition metal complex corresponds to the general formula:

wherein
   M is a transition metal ion;
   $n_1$, $n_2$, $n_3$, $n_4$ can be the same or different and can be 0 or 1;
   $D_1$, $D_2$, $D_3$, and $D_4$ can be the same or different and can be C, N, O, S, or P;
   $B_{1a}$, $B_{1b}$, $B_{2a}$, $B_{2b}$, $B_{3a}$, $B_{3b}$, $B_{4a}$, and $B_{4b}$ can be the same or different and can be H, F, $CH_3$, alcohol, allyl, amine, styrene, methacrylate, acrylate, vinyl, vinyl ether, vinyl acetate, trialkoxysilane, dialkoxycholorosilane and epoxy;
   $X_1$, $X_2$, $X_3$, and $X_4$ can be the same or different and can be N, C, H, or B;
   $A_{1a}$, $A_{1b}$, $A_{2a}$, $A_{2b}$, $A_{3a}$, $A_{3b}$, $A_{4a}$, and $A_{4b}$ call be the same or different and can be H, F, $NH_3$, $NO_2$, $CO_2^-$, $CO_2H$, $CO_2R$, alcohol, allyl, styrene, methacrylate, acrylate, vinyl, vinyl ether, vinyl acetate, trialkoxysilane, dialkoxycholorosilane and epoxy;

$Y_{1a}$, $Y_{1b}$, $Y_{2a}$, $Y_{2b}$, $Y_{3a}$, $Y_{3b}$, $Y_{4a}$, and $Y_{4b}$ may be the same or different, and can be C or O; and, $C_{1a}$, $C_{1b}$, $C_{2a}$, $C_{2b}$, $C_{3a}$, $C_{3b}$, $C_{4a}$, $C_{4b}$, $C_{5a}$, $C_{5b}$, $C_{6a}$, $C_{6b}$, $C_{7a}$, $C_{7b}$, $C_{8a}$, and $C_{8b}$ can be the same or different and can be H, F, $NH_3$, $NO_2$, $CO_2^-$, $CO_2H$, $CO_2R$, alcohol, allyl, styrene, methacrylate, acrylate, vinyl, vinyl ether, vinyl acetate, trialkoxysilane, dialkoxycholorosilane and epoxy.

8. The polymer of claim 6 wherein M is nickel(II), $D_1$, $D_2$, $D_3$, and $D_4$ are N, $Y_{1a}$, $Y_{1b}$, $Y_{2a}$, $Y_{2b}$, $Y_{3a}$, $Y_{3b}$, $Y_{4a}$ and $Y_{4b}$ are C, $n_1$ and $n_3$ are 1, $n_2$ and $n_4$ are 0, $X_1$ and $X_3$ are N, $A_{1a}$ and $A_3$ are styrene, vinyl, amine or carboxyl, and $A_{1a}$ and $A_{3a}$ are electron lone pairs.

9. The polymer of claim 6 wherein the biogenic amine is selected from the group consisting of cadaverine, putrescine and histamine.

10. A food container comprising the polymer of claim 6.

11. A sensor for detecting the presence of biogenic amine in, on or in association with a food which comprises a polymer and a support structure having a surface, the polymer being attached to the support structure as a coating thereon, wherein the polymer is formed by the steps of:
copolymerizing a polyazamacrocylic transition metal complex possessing one or more polymerizable groups, monomer and crosslinking agent,
wherein said polymer undergoes a detectable color change upon exposure to a biogenic amine.

12. The sensor of claim 11 wherein the structure comprises a plastic sheet, film or tray which is utilized in the packaging of food products.

13. The sensor of claim 11 wherein the structure is an optical fiber.

14. The sensor of claim 11 wherein the biogenic amine is selected from the group consisting of cadaverine, putrescine and histamine.

15. The sensor of claim 11 wherein the polyazamacrocyclic transition metal complex is first reacted with a target molecule comprising biogenic diamine prior to copolymerizing the complex, monomer and crosslinking agent, and thereafter the target molecule is removed from the polymer to provide a molecularly imprinted polymer which selectively binds to the target molecule and undergoes a detectable color change when the target molecule binds thereto.

16. The sensor of claim 11 wherein the color change is visible.

17. The sensor of claim 11 wherein the color change is from yellow to blue/violet.

18. A method for detecting food spoilage, comprising:
providing a polymer comprising the reaction product of a polyazamacrocyclic transition metal complex possessing one or more polymerizable groups, monomer and crosslinking agent,
exposing the polymer to an environment containing food such that fluids from the food come in contact with the polymer,
wherein said polymer undergoes a detectable color change upon exposure to biogenic amine which is indicative of food spoilage.

19. The method of claim 18 wherein the the biogenic amine is selected from the group consisting of cadaverine, putrescine and histamine.

20. The method of claim 18 wherein the polyazamacrocyclic transition metal complex is first reacted with a target molecule comprising biogenic diamine prior to copolymerizing the complex, monomer and crosslinking agent, and thereafter the target molecule is removed from the polymer to provide a molecularly imprinted polymer which selectively binds to the target molecule and undergoes a detectable color change when the target molecule binds thereto.

21. The method of claim 18 wherein the color change is visible.

22. The method of claim 18 wherein the color change is from yellow to blue/violet.

23. The method of claim 18 wherein the wherein the polyazamacrocyclic transition metal complex corresponds to the general formula:

wherein

M is a transition metal ion;

$n_1$, $n_2$, $n_3$, $n_4$ can be the same or different and can be 0 or 1;

$D_1$, $D_2$, $D_3$, and $D_4$ can be the same or different and can be C, N, O, S, or P;

$B_{1a}$, $B_{1b}$, $B_{2a}$, $B_{2b}$, $B_{3a}$, $B_{3b}$, $B_{4a}$, and $B_{4b}$ can be the same or different and can be H, F, $CH_3$, alcohol, allyl, amine, styrene, methacrylate, acrylate, vinyl, vinyl ether, vinyl acetate, trialkoxysilane, dialkoxycholorosilane and epoxy;

$X_1$, $X_2$, $X_3$, and $X_4$ can be the same or different and can be N, C, H, or B;

$A_{1a}$, $A_{1b}$, $A_{2a}$, $A_{2b}$, $A_{3a}$, $A_{3b}$, $A_{4a}$, and $A_{4b}$ can be the same or different and can be H, F, $NH_3$, $NO_2$, $CO_2^-$, $CO_2H$, $CO_2R$, alcohol, allyl, styrene, methacrylate, acrylate, vinyl, vinyl ether, vinyl acetate, trialkoxysilane, dialkoxycholorosilane and epoxy;

$Y_{1a}$, $Y_{1b}$, $Y_{2a}$, $Y_{2b}$, $Y_{3a}$, $Y_{3b}$, $Y_{4a}$, and $Y_{4b}$ may be the same or different, and can be C or O; and, $C_{1a}$, $C_{1b}$, $C_{2a}$, $C_{2b}$, $C_{3a}$, $C_{3b}$, $C_{4a}$, $C_{4b}$, $C_{5a}$, $C_{5b}$, $C_{6a}$, $C_{6b}$, $C_{7a}$, $C_{7b}$, $C_{8a}$, and $C_{8b}$ can be the same or different and can be H, F, $NH_3$, $NO_2$, $CO_2^-$, $CO_2H$, $CO_2R$, alcohol, allyl, styrene, methacrylate, acrylate, vinyl, vinyl ether, vinyl acetate, trialkoxysilane, dialkoxycholorosilane and epoxy.

24. The method of claim 23 wherein M is nickel(II), $D_1$, $D_2$, $D_3$, and $D_4$ are N, $Y_{1a}$, $Y_{1b}$, $Y_{2a}$, $Y_{2b}$, $Y_{3a}$, $Y_{3b}$, $Y_{4a}$, and $Y_{4b}$ are C, $n_1$ and $n_3$ are 1, $n_2$ and $n_4$ are 0, $X_1$ and $X_3$ are N, $A_{1a}$ and $A_{3a}$ are styrene, vinyl, amine or carboxyl, and $A_{1a}$ and $A_{3a}$ are electron lone pairs.

25. A sensor for detecting the presence of biogenic amine in, on or in association with a food which comprises a molecularly imprinted polymer and a support structure having a surface to support the polymer, wherein the polymer comprises the reaction product of a polyazamacrocyclic transition metal complex possessing one or more polymerizable groups; a monomer; and an optional crosslinking agent, wherein said polymer exhibits selective binding affinity for said biogenic amine and undergoes a detectable change in absorption or emission of electromagnetic radiation upon exposure to said biogenic amine.

26. The sensor of claim 25 wherein the biogenic amine is selected from the group consisting of cadaverine, putrescine and histamine.

27. The sensor of claim 25 wherein the polymer undergoes a detectable change in absorption or emission of electromagnetic radiation in the visible region.

* * * * *